(12) United States Patent
Batchelor et al.

(10) Patent No.: US 11,937,867 B2
(45) Date of Patent: *Mar. 26, 2024

(54) VESSEL SEALING DEVICE

(71) Applicant: GYRUS ACMI, INC., Southborough, MA (US)

(72) Inventors: Kester Julian Batchelor, Mound, MN (US); Jeffrey Nelson, Plymouth, MN (US); Huisun Wang, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 596 days.

This patent is subject to a terminal disclaimer.

(21) Appl. No.: 17/080,234

(22) Filed: Oct. 26, 2020

(65) Prior Publication Data
US 2021/0038294 A1 Feb. 11, 2021

Related U.S. Application Data

(63) Continuation of application No. 15/815,827, filed on Nov. 17, 2017, now Pat. No. 10,842,552.

(51) Int. Cl.
*A61B 18/14* (2006.01)
*A61B 17/29* (2006.01)
(Continued)

(52) U.S. Cl.
CPC .......... *A61B 18/1445* (2013.01); *A61B 17/29* (2013.01); *A61B 2017/00022* (2013.01);
(Continued)

(58) Field of Classification Search
CPC ................ A61B 18/1445; A61B 17/29; A61B 2017/00022; A61B 2017/00557;
(Continued)

(56) References Cited

U.S. PATENT DOCUMENTS 3,503,396 A 3/1970 Pierie et al.
3,503,398 A 3/1970 Fogarty et al.
(Continued)

FOREIGN PATENT DOCUMENTS

EP 2604210 A1 6/2013
WO WO-02067797 A2 9/2002

OTHER PUBLICATIONS

"U.S. Appl. No. 15/815,827, Non Final Office Action dated Mar. 16, 2020", 7 pgs.
(Continued)

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

A surgical device that includes a first support member extending along a longitudinal axis; a bladder located on the first support member; a first sealing member located on the bladder; and a second sealing member located on the bladder. The sealing member is located on one side of the longitudinal axis; and the second sealing member is located on another side of the longitudinal axis. The bladder is inflatable, and inflating the bladder changes a position of the first sealing member, the second sealing member, or both relative to the first support member.

20 Claims, 3 Drawing Sheets

(51) Int. Cl.
 *A61B 17/00* (2006.01)
 *A61B 18/00* (2006.01)

(52) U.S. Cl.
 CPC ........... *A61B 2017/00557* (2013.01); *A61B 2017/2926* (2013.01); *A61B 2017/2932* (2013.01); *A61B 2018/00226* (2013.01); *A61B 2018/0063* (2013.01); *A61B 2018/00696* (2013.01); *A61B 2018/1455* (2013.01)

(58) Field of Classification Search
 CPC .... A61B 2017/2926; A61B 2017/2932; A61B 2018/00226; A61B 2018/0063; A61B 2018/00696; A61B 2018/1455
 See application file for complete search history.

(56) References Cited

U.S. PATENT DOCUMENTS

| | | | |
|---|---|---|---|
| 3,515,139 A | 6/1970 | Mallina | |
| 3,538,917 A | 11/1970 | Selker | |
| 3,746,002 A | 7/1973 | Haller | |
| 4,708,140 A | 11/1987 | Baron | |
| 4,800,879 A | 1/1989 | Golyakhovsky et al. | |
| 5,258,005 A | 11/1993 | Christian | |
| 5,454,826 A | 10/1995 | Ueda | |
| 5,626,607 A | 5/1997 | Malecki et al. | |
| 5,647,871 A | 7/1997 | Levine et al. | |
| 6,086,586 A | 7/2000 | Hooven | |
| 6,206,896 B1 | 3/2001 | Howell et al. | |
| 6,837,885 B2 | 1/2005 | Koblish et al. | |
| 6,966,908 B2 | 11/2005 | Maguire et al. | |
| 7,276,068 B2 | 10/2007 | Johnson et al. | |
| 7,491,202 B2 | 2/2009 | Odom et al. | |
| 7,556,628 B2 | 7/2009 | Utley et al. | |
| 10,842,552 B2 | 11/2020 | Batchelor et al. | |
| 2008/0275445 A1 | 11/2008 | Every et al. | |
| 2009/0182333 A1* | 7/2009 | Eder | A61B 18/1442 606/51 |
| 2011/0087337 A1 | 4/2011 | Forsell | |
| 2011/0301604 A1 | 12/2011 | Horner et al. | |
| 2011/0306968 A1 | 12/2011 | Beckman et al. | |
| 2012/0296232 A1 | 11/2012 | Ng | |
| 2013/0090649 A1 | 4/2013 | Smith et al. | |
| 2014/0288541 A1* | 9/2014 | Eshkol | A61B 17/30 606/7 |
| 2014/0309671 A1 | 10/2014 | Basic et al. | |
| 2015/0164571 A1 | 6/2015 | Saadat | |
| 2016/0022354 A1 | 1/2016 | Goshayeshgar | |
| 2017/0348042 A1* | 12/2017 | Drochner | A61B 18/1445 |
| 2019/0151010 A1 | 5/2019 | Batchelor et al. | |

OTHER PUBLICATIONS

"U.S. Appl. No. 15/815,827, Notice of Allowance dated Jul. 24, 2020", 5 pgs.

"U.S. Appl. No. 15/815,827, Response filed Jun. 11, 2020 to Non Final Office Action dated Mar. 16, 2020", 8 pgs.

* cited by examiner

VESSEL SEALING DEVICE

FIELD

These teachings relate to a surgical device for effecting an anatomical feature.

BACKGROUND

Forceps are plier-like devices that include a jaw assembly. The jaw assembly includes a pair of opposing jaws. One or both of the jaws can be moved between an open and closed configuration, and can be used to effect an anatomical feature. For example, the forceps can be used to grip, capture, grasp, manipulate, pull, constrict, cut, and/or dissect the anatomical feature. Some forceps also include electrosurgical capabilities so that the anatomical feature can be electrically effected (e.g., cut and/or coagulated) with one or more therapy currents. U.S. Pat. No. 7,276,068 and U.S. Patent Application Publication Number 2011/0301604 disclose examples of devices having a jaw assembly.

When forceps are moved into the closed configuration, one or both of the jaws typically pivot relative to each other to apply a clamping force on the anatomical feature that is located between the jaws. This pivoting action typically results in application of uneven clamping forces on the anatomical feature across a length of the jaw assembly. For example, higher clamping forces are applied on the anatomical feature with a proximal portion of the jaws and lower clamping forces are applied on the anatomical feature with the distal portion of the jaws.

Higher clamping forces may undesirably over pressurize the anatomical feature, which may result in wall ruptures in the anatomical feature. Higher clamping forces may also undesirably push or "squirt" the anatomical feature along a length of the jaws. Lower clamping forces may result in poor vessel sealing or effecting.

It would be desirable to have a jaw assembly that can provide a generally constant or uniform clamping force across an entire length of the jaws.

SUMMARY

The surgical device according to these teachings is capable of applying a generally constant or uniform clamping force on an anatomical feature along a length of the jaws or the jaw assembly, so that chances of over pressuring or rupturing an anatomical feature are reduced. Moreover, after a consistent or uniform clamping force is applied on the anatomical feature with the device according to these teachings, chances of the anatomical feature moving or squirting towards the distal end of the jaw assembly are reduced. This advantageously provides the surgeon with better control of the anatomical feature during a surgical procedure.

The length of the jaw or jaw assembly is defined between a proximal end or proximal portion of a jaw or jaw assembly and a distal end or distal portion of the jaw or jaw assembly. A constant or uniform clamping force or pressure means that the clamping force or pressure applied on an anatomical feature located between the jaws or jaw assembly at a proximal end or proximal portion of the jaw assembly is generally the same as the clamping force applied on the anatomical feature located between the jaws or jaw assembly at a distal end or distal portion of the jaw assembly.

Typically, in forceps devices that pivot between an open and closed position by way of one or both jaws moving, pivoting, or tipping towards one another, the clamping force or pressure at the proximal end or proximal portion of the jaws or jaw assembly is higher or larger than the clamping force or pressure at the distal end or distal portion of the jaws or jaw assembly. These teachings remedy this difference in clamping force or pressure across a length of the jaws or jaw assembly by proving one or more bladders on one or both of the jaws or support members. By inflating the one or more bladders, a generally constant or uniform clamping force can be applied on an anatomical feature along a length of the jaws or the jaw assembly.

These teachings provide a jaw assembly that includes a pair of opposing jaws. One or both of the jaws comprise a support member. One or both of the jaws comprise a bladder located on the support member. One or both of the jaws comprise one or more sealing members located on the one or more bladder such that bladder is at least partially sandwiched between the one or more sealing members and the support member.

The bladder is inflatable and deflatable. Inflating the bladder provides for the one or more sealing members located on the bladder to move or displace relative to the support member or the opposing jaw without moving or pivoting the jaw assembly. Moving or displacing the one or more sealing members towards the opposing jaw without moving or pivoting the jaw functions to provide a generally constant and uniform clamping forces across an entire length of the jaws. That is, the clamping forces applied on the anatomical feature by a proximal end or throat end of the jaw assembly is generally the same as the gripping force applied on the anatomical feature by the middle or distal end of the jaw assembly.

More specifically, by inflating the bladder, the one or more sealing members are moved or displaced towards the opposing jaw in a generally parallel manner. This means that while moving the jaw assembly into the closed configuration, inflating the bladder results in the gap defined between a proximal end of the one or more sealing members and a proximal end of the opposing jaw being generally the same as a gap defined between a distal end of the one or more sealing members and a distal end of the opposing jaw. This is in contrast to traditional pivoting jaws, where during movement of the jaw assembly into the closed configuration, the gap defined between a proximal end of the one or more sealing members and a proximal end of the opposing jaw is smaller than a gap defined between a distal end of the one or more sealing members and a distal end of the opposing jaw The surgical device according to these teachings may also include a cut blade. The cut blade may be located in between the jaws, and within a blade slot that is defined in one or both jaws. The cut blade may be advanced through tissue clamped between the jaws. By having a jaw assembly that can apply a consistent gripping pressure along a length of the jaws, the cut blade may more easily and consistently cut or slice through an anatomical feature, as opposed to cutting or slicing through tissue that is clamped between jaws with varying or inconsistent clamped forces along a length of the jaws.

These teachings provide a surgical device that includes a first support member comprising a blade slot; a blade located in the blade slot; a bladder located on the first support member; a first sealing member located on the bladder, the first sealing member is located on one side of the blade slot; and a second sealing member located on the bladder, the second sealing member is located on another side of the blade slot. The bladder is inflatable, and inflating the bladder changes a position of the first sealing member, the second sealing member, or both relative to the first support member.

These teachings also provide surgical device that includes a first support member extending along a longitudinal axis; a bladder located on the first support member; a first sealing member located on the bladder; and a second sealing member located on the bladder. The sealing member is located on one side of the longitudinal axis; and the second sealing member is located on another side of the longitudinal axis. The bladder is inflatable, and inflating the bladder changes a position of the first sealing member, the second sealing member, or both relative to the first support member.

DETAILED DESCRIPTION

These teachings provide a surgical device. The surgical device may be any device or instrument for effecting an object or anatomical feature. Effecting may mean, for example, holding, manipulating, engaging, moving, grasping, gripping, constricting, pushing, pulling, cutting, tearing, coagulating, sealing, cauterizing, dissecting, fulgurating, or a combination thereof an object or anatomical feature. The anatomical feature may be any anatomical feature, such as a vessel, tissue, vein, artery, the like, or a combination thereof.

The surgical device can be used in virtually any procedure, whether medically related or not. In medical procedures, the surgical device can be used in open procedures, laparoscopic procedures, or both.

The surgical device can be used with or without power. When used with power, one or more electrical currents, therapies, and/or signals may be provided to the surgical device from a power source or generator to electrically effect an anatomical feature. The power source may be a generator. The power source may be of the type described in U.S. Pat. No. 7,282,048B2, the teachings of which are hereby incorporated by reference herein for all purposes.

The one or more electrical currents, therapies, and/or signals provided by the power source to the device or to the one or more sealing members may be monopolar energy, bipolar energy, blended energy, or a combination thereof.

The surgical device may be an electrosurgical device. The surgical device may be forceps. The surgical device may be electrosurgical forceps. The surgical device may be a spatula. The surgical device may be an electrosurgical spatula.

The surgical device comprises a hand piece. The hand piece may function to be held by a user. The hand piece may include one or more user controls for operating, actuating, moving, reciprocating, opening, closing, retracting, extending, rotating, inflating, deflating, and/or manipulating one or more of the jaws, the jaw assembly, one or both of the support members, one or more of the bladders, one or more of the sealing member(s), the cut blade, or a combination thereof.

The one or more user controls may include one or more triggers, wheels, levers, buttons, knobs, the like, or a combination thereof. A user control may also include a foot pedal.

For example, manipulation or movement of the lever may function to move the jaw assembly (i.e., to move one or both of the jaws) from an open configuration to a closed configuration, and vice versa. For example, manipulation or movement of the wheel may function to rotate the jaw assembly about a longitudinal axis of the jaw assembly, the tubular member, or both. For example, manipulation or movement of the trigger may function to move, translate, or reciprocate the cut blade along a longitudinal axis of the cut blade, the tubular member, the jaw assembly, or a combination thereof. For example, manipulation or movement of the button may function to apply a therapeutic current or signal from the power supply to the jaw assembly, one or both of the jaws, one or more of the sealing members, or a combination thereof. For example, manipulation or movement of the button or foot pedal may function to inflate or deflate one or more of the bladders.

The surgical device may comprise an introducer. The introducer may function to permit a portion of the device to be inserted into a patient or the anatomy, while a portion of the device remains outside of the patient or anatomy. The introducer may be configured to be inserted into the anatomy through a trocar.

The introducer may be a tubular member. The introducer may be an elongated member that extends along a longitudinal axis. The proximal end of the introducer may be connected to the hand piece. The distal end of the introducer may define a mouth or opening (i.e., a distal opening). The introducer may be at least partially hollow and may define therein an inner portion. The hollow or inner portion of the introducer, the distal opening, or both, may be sufficiently sized so that one or more jaws, a jaw assembly, a cut blade, or a combination thereof can be received in and/or moved (i.e., linearly or rotationally about the longitudinal axis) inside the tubular member. The introducer may be substantially straight; may include one or more angles, bends or arcs; or a combination thereof. The introducer may be substantially rigid, substantially flexible, substantially resilient, or a combination thereof.

In some configurations, the introducer can be moved (i.e., axially, distally, proximally, rotationally or a combination thereof) relative to the hand piece. The introducer can be moved by manipulating one of the user controls on the hand piece. The introducer may be moved distally towards the jaw assembly, proximally towards the hand piece, or both so that the jaw assembly can be moved between a closed configuration and an open configuration, respectively. More specifically, by manipulating one or more user controls, the introducer can be moved in a first direction (i.e., distally away from the hand piece) and up, over and/or onto the arcuate portions of one or both of the jaws so that the jaw assembly can be moved into a closed or gripping configuration. By manipulating one or more user controls, the introducer can be moved in a second direction (i.e., proximally towards the hand piece) so that the introducer moves off of the arcuate sections, thus allowing one or both of the jaws to relax or flex into an open, steady state configuration. In this type of configuration, the jaw assembly is preferably fixed to the hand piece and does not move distally or proximally relative to the hand piece.

Additionally, or alternatively, the introducer may be fixed relative to the hand piece and the jaw assembly may be moveable relative to the hand piece. In this configuration, by manipulating one or more user controls, the jaw assembly can be moved in a first direction (i.e., proximally towards the hand piece) so that the introducer or the mouth or opening of the introducer acts on the arcuate sections of one or both of the jaws so that the jaw assembly can be moved into a closed configuration. By manipulating one or more user controls, the jaw assembly can be moved in a second direction (i.e., distally away the hand piece) so that the introducer or the mouth or opening of the introducer is moved off of the arcuate sections of one or both of the jaws so that the jaw assembly can relax or flex into an open configuration. Alternatively, the jaw assembly may be akin to tweezers, and the jaws can be manually moved into the closed configuration by applying a pressing force on one or both of the jaws with a user's fingers. Releasing the pressing force from one or both of the jaws allows for the jaws to relax into a steady state open configuration.

The surgical device may include a jaw assembly. The jaw assembly may be configured to perform one or more effecting functions. For example, the one or more effecting functions may include: capturing an object or anatomical feature; grasping an object or anatomical feature; providing a clamping force to secure an object or anatomical feature; providing retraction of an object or anatomical feature; providing a compression force across an object or anatomical feature captured in the jaw assembly; or a combination thereof. The jaw assembly may be used in electrosurgery to perform one or more electrically effecting functions, such as cutting, coagulating, cauterizing, dissecting, and/or fulgurating an object anatomical feature.

The jaw assembly may be moved between a closed configuration and an open configuration. The jaw assembly may include a hinge or cam or other pivot mechanism for pivoting one or both of the jaws of the jaw assembly between the open and closed configurations.

For example, the jaw assembly may include one jaw that is moveable relative an opposing, fixed jaw that does not move. The moveable jaw can be moved towards or away from the fixed jaw by manipulating one or more of the user controls to move the jaw assembly into the closed or open configuration, respectively. In such a configuration, the jaw assembly can also be moved into a closed configuration by inflating one or more bladders. The jaw assembly can be moved into the open configuration by deflating one or more bladders.

For example, the jaw assembly may comprise a pair of opposing jaws that are both moveable towards and away from each other. Both jaws can be moved towards or away from each other by manipulating one or more of the user controls to move the jaw assembly into the closed or open configuration, respectively. In such a configuration, the jaw assembly can also be moved into a closed configuration by inflating one or more bladders. The jaw assembly can be moved into the open configuration by deflating one or more bladders.

Alternatively, the jaw assembly may comprise a pair of opposing jaws that are both fixed and unable to move relative to each other. In such a configuration, the jaw assembly may be moved into the closed or gripping configuration by inflating the one or more bladders carried on one or both of the jaws. In such a configuration, the jaw assembly may be moved into the open configuration by deflating the one or more bladders carried on one or both of the jaws.

The closed configuration may be defined as a position of the jaws or the bladder or the sealing member(s) where virtually no gap, or only a slight gap, exists between the opposing jaws or bladders or sealing members. In the closed configuration, a clamping force may be higher or larger than a clamping force when the jaws are in the open configuration. In the closed configuration, a clamping force applied on an anatomical feature by a proximal end or proximal portion or throat of the jaw assembly is generally the same as a clamping force applied on the anatomical feature by a distal end of the jaws or jaw assembly.

The open configuration may be defined as a position of the jaws or the bladder or the sealing member(s) where a gap exists or is defined between the opposing jaws or bladder or sealing members. In the open configuration, a clamping force may be lower or smaller than a clamping force when the jaws are in the closed configuration.

While the jaw assembly is in the open configuration, the closed configuration, or in a position or configuration therebetween, one or more of the bladders can be inflated and/or deflated.

While the jaw assembly is in the open configuration, the closed configuration, or in a position or configuration therebetween, the jaw assembly can be rotated relative to the hand piece or the introducer by manipulating or moving one or more of the controls on the hand piece. Rotating the jaw assembly may provide for a user to alter an orientation or approach of the jaw assembly relative to an anatomical feature without having to twist or adjust the hand piece into a difficult or uncomfortable position, for example.

The term or description of a jaw assembly as used herein may also include only a single jaw or a single support member. A device having a single jaw or a single support member may be a spatula. A surgical device that is a spatula according to these teachings may have one or more bladders according to any of the teachings herein, and one or more sealing members according to any of the teachings herein located on the one or more bladders. The one or more sealing members and the one or more bladders of the spatula may be located only one side of the jaw or support member, or one or more sealing members and the one or more bladders may be located on both sides of the jaw or support member of the spatula. This means that the one or more bladders and/or sealing members are located on opposing surfaces—that is, the one or more bladders and sealing members do not face each other. This means that the one or more bladders and sealing members are located on different planes; the planes being offset from each other by a thickness of the support member. This means that one bladder and/or sealing member can be located on one side of a plane and one bladder and/or sealing member can be located on another side of the plane. This means that one bladder and/or sealing member may face in a normal direction relative to a plane, and one bladder and/or sealing member may face in a normal direction relative to a plane, wherein the normal directions oppose each other. Normal means perpendicular to the plane.

A spatula may be used to separate tissue planes. During use, the spatula, or the support member(s) comprising the one or more bladders and the one or more sealing members are placed between tissue planes and move to separate or pry apart tissue planes. This may also be referred to in the art as blunt dissection. During blunt dissection, the one or more sealing members may function to stop bleeding in tissue by pressing the one or more sealing members against the tissue and passing a therapy current from the generator to the bleeding tissue to coagulate the tissue. The planes may be separated by manually moving the spatula, by inflating one or both of the bladders, deflating one or more of the bladders, or a combination thereof.

The surgical device and/or the jaw assembly may comprise one or more jaws. The surgical device and/or the jaw assembly may comprise exactly two jaws.

The one or more jaws may be moved, adjusted, manipulated, repositioned, opened, closed, rotated, advanced, retracted, or otherwise articulated, individually or together in unison, by moving or manipulating one or more of the user controls on the hand piece.

The jaws may be arranged to oppose one another. The jaws may include a first jaw, a second jaw, an upper jaw, a lower jaw, or a combination thereof. The opposing jaws may be identical in structure. Alternatively, the two opposing jaws need not be identical in structure. For example, both of the jaws may comprise one or more bladders, or one of the jaws may include a bladder and the other jaw may be free of a bladder. For example, both of the jaws may comprise a blade slot, or only one of the jaws may comprise a blade slot, and the other jaw may be free of a blade slot. For example, both of the jaws may comprise one or more sealing members, or only one of the jaws may include one or more sealing members, and the other jaw may be free of sealing members. For example, one of the jaws may have one of the structures disclosed herein, and another one of the jaws may have another one of the structures disclosed herein.

The one or more jaws may be fabricated from a material that is suitable for use in medical procedures, and is flexible, yet strong. For example, the one or more jaws may be made from sheet metal or wire. The one or more jaws may be formed by any suitable process, such as stamping, metal injection molding (MIM), or plastic injection molding, for example. The one or more jaws may be fabricated from a material that can pass current so that one or more of the jaws can be used in electrosurgery.

One or both of the jaws, or sections thereof, may be electrically conductive. One or both of the jaws, or sections thereof, may be non-electrically conductive. The one or more jaws may be thermally insulating so that a thermal barrier can be provided between the jaws, the jaw assembly, or both. A thermally insulating jaw may be preferred in some applications so that thermal spread is limited or reduced. One or more sections of the jaws may be covered or coated in an insulating material so that electrical shorts can be prevented if the jaws come into contact with one another or another object or feature of the instrument or surrounding environment.

One or more of the jaws may include a support member. The support member may be a base of the jaw. The support member or a support surface thereof may function to provide a surface or structure for the one or more bladders to be located on or attached to. The support member may be an insulator or electrically non-conductive. The support member may be a bottom portion of the jaw. The support member may comprise a notch or cutout (i.e., blade slot) for receiving or accommodating a cut blade. The support member may be substantially solid and be free of any notches, slots, or blade slots.

The support member may comprise a support surface. The support surface may be any surface of the support member on which one or more bladders are located. The support surface may be on only one side of a blade slot, on both sides of a blade slot, at a front or distal portion of a blade slot, or a combination thereof. The support surface may be on only one side of the support member. The support surface may be on both sides of the support member.

One or both of jaws or support members may include a blade slot. The blade slot may function to provide a passageway or area for a cut blade or other medical instrument or feature to be located, moved, rotated and/or reciprocated. The blade slot may function to allow the cut blade to effect an anatomical feature without the cut blade contacting the one or more bladders, the one or more sealing members, other portions of the jaw or support member, or a combination thereof.

The blade slot may be centered upon a central plane or central longitudinal axis of the corresponding jaw or support member, or the blade slot may be offset or laterally spaced apart to one side of the jaw or support member from a central longitudinal axis of the jaw or support member.

The blade slot may include one or more walls that project away from the base or support surface of the support member. The one or more walls may be fabricated from the same material as the support member. The one or more walls may be fabricated from an insulator or non-conductive material to prevent accidental shorting or arcing if an energized sealing member and/or cut blade contact the one or more walls.

For example, the blade slot may include one or more longitudinal side walls that extend along a length of the blade slot, the jaw, or support member. The one or more longitudinal side walls may function to prevent the cut blade located within the blade slot from inadvertently contacting and potentially damaging the one or more bladders, or the one or more longitudinal sections of the bladder, the one or more sealing members, the one or more longitudinal sections of the sealing member, or a combination thereof.

For example, the blade slot may include a front or distal wall that is arranged generally perpendicular to the one or more longitudinal side walls of the blade slot. The front or distal wall of the blade slot may function to prevent the cut blade or a distal end of the cut blade from inadvertently contacting and potentially damaging the one or more bladders, a distal or nose section of the bladder, the one or more sealing members, a distal or nose section of the sealing member, or a combination thereof.

The blade slot may have an L-shaped that includes a front or distal wall and one longitudinal side wall. The blade slot may have a U-shape that includes a front or distal wall and two longitudinal side walls that are spaced apart from one another. The blade slot may also only include one side or longitudinal wall. The blade slot may also only include the front or distal wall.

The device may comprise one or more cut blades. The cut blade may function to cut an anatomical feature. The cut blade may be a cutting blade or a scalpel. The cut blade may be connected to the power source so that the cut blade can be used to electrically effect an anatomical feature by passing an electrical therapy current to or through the anatomical feature. The cut blade may not be connected to the power source or is electrically isolated from the power source; thus, the cut blade may be free from passing an electrical therapy current to effect an anatomical feature. Thus, the cut blade may be a cold cut blade or a mechanical cut blade.

The cut blade may be moved or reciprocated or extended or retracted within the blade slot by moving or manipulating one or more of the user controls. The cut blade can be moved or extended to cut an anatomical feature captured between the jaw assembly when the jaw assembly is in a closed or clamping configuration. The cut blade may cut an anatomical feature after the anatomical feature is clamped and/or coagulated or sealed between the jaws of the jaw assembly.

The cut blade may be centered along or about a longitudinal axis defining the blade slot. Alternatively, the cut blade may be offset to one side of the blade slot (i.e., laterally offset from the center slot axis).

The surgical device, the jaw assembly, the one or more jaws, the one or more support members, or a combination thereof may comprise one or more sealing members.

The one or more sealing members may function to effect an anatomical feature. For example, one or more sealing members may be used to capture, grip, grasp, and/or manipulate an object or anatomical feature; provide a clamping force to secure an object or anatomical feature; provide retraction of an object or anatomical feature; provide a compression or gripping or clamping force across an object or anatomical feature; or a combination thereof. The one or more sealing members may be connected to the power source and used in electrosurgery to cut, coagulate, cauterize, dissect, and/or fulgurate an object or anatomical feature.

The one or more sealing members may be pressed against tissue or anatomical feature while passing a therapy current from the one or more sealing members to the tissue to coagulate the tissue or anatomical feature. This may be done during blunt dissection with a surgical device that is a spatula, for example. An anatomical feature may be placed between the sealing members of a jaw assembly, and the anatomical feature can be treated or effected by occluding the sides of the vessel to block blood flow.

The surface of the one or more sealing members may be generally smooth. Alternatively, the surface of the one or more sealing members may have a texture or teeth to aid in gripping, pulling, or clamping of an anatomical feature.

Each of the one or more sealing members may be discretely and individually electrically connected to the power source via one or more wires, connections, conductors, and/or plugs. Two or more sealing members may be electrically disconnected from one another, which means that the sealing members are not in electrical contact with one another, and are in electrical communication with opposing poles of the power source or generator.

One or more of the sealing members may have a first polarity (e.g. '−') and one or more of the sealing members may have a second polarity (e.g. '+'). For example, one or more sealing members located on one side of the blade slot or longitudinal axis of the jaw or support member may have a first polarity, and one or more sealing members located on the other side of the blade slot or longitudinal axis of the jaw or support member may have a second polarity. For example, one or more sealing members located on one of the jaws or support member may have a first polarity, and one or more sealing members located on the opposing jaw or support member may have a second polarity. For example, one or more sealing members located on one side of the jaws or support member may have a first polarity, and one or more sealing members located on an opposing side of the same jaw or support member may have a second polarity. For example, one or more sealing members located on one side of the support member of a spatula may have a first polarity, and one or more sealing members located on an opposing side of the same support member may have a second polarity.

The one or more sealing members may be fabricated from a suitable material such as sheet metal. The one or more sealing members may have a constant thickness or the thickness may vary between a proximal and distal end thereof. The thickness of the one or more sealing members may be on the order of approximately 0.02 mm or more, 0.04 mm or more, 0.05 mm or more, 0.10 mm or more, 0.20 mm or more, 0.30 mm or more, 0.40 mm or more, 0.50 mm or more, 0.60 mm or more, 0.70 mm or more, 0.75 mm or more. The thickness of the one or more sealing members may be on the order of approximately 1.00 mm or less, 0.90 mm or less, 0.80 mm or less, 0.75 mm or less. Preferably, the thickness of the one or more sealing members is between about 0.05 mm and approximately 0.75 mm.

The one or more sealing members may be located on or attached to the one or more bladders. This means that the bladder is sandwiched between the one or more sealing members and the support member that carries that one or more bladders.

Two or more of the sealing members may be located on a common plane. This means that the relative distance between the support member and each of the sealing members is generally the same.

The two or more sealing members may be located on different planes relative to one another. This means that the relative distance between the support member and each of the sealing members is different or the sealing members are offset from the support member relative to one another. Different planes may also refer to one or more sealing members being located on one jaw or support member compared to one or more sealing members being located on another jaw or support member. Different planes may also refer to one or more sealing members being located on side of a one jaw or support member compared to one or more sealing members being located on another side of the same jaw or support member.

The one or more sealing members may have any suitable shape.

For example, the one or more sealing members may be generally L-shaped. That is, each of the one or more sealing members may comprise a longitudinal section that extends along a length of the jaw or support member. The sealing member may comprise a nose or distal section. The nose or distal section is located at a distal end of the longitudinal member, and may be generally perpendicular to the longitudinal section so that the sealing member is L-shaped. The nose or distal section may function as a bridge or connector between the two longitudinal members of the sealing member.

For example, the one or more sealing members may be generally U-shaped. That is, each of the one or more sealing members may comprise two generally parallel longitudinal sections that extends along a length of the jaw or support member. The sealing member may comprise a nose or distal section. The nose or distal member is connected to the distal ends of the longitudinal sections, and may be generally perpendicular to the longitudinal members so that the sealing member is u-shaped.

For example, the one or more sealing members may comprise only an elongated generally linear member. That is, each of the one or more sealing members may comprise only a longitudinal section that extends along a length of the jaw or support member. For example, the one or more sealing members may comprise a curved or irregularly shaped member The one or more sealing members may be electrode dots on a surface of the bladder. The electrode dots may be applied to the bladder by painting, vapor deposition, chemical coating, adhesively bonding or other similar techniques.

Each of the dots may be individually electrically connected to a pole of the generator. Alternatively, one or more of the dots may be electrically connected to a same pole of the generator.

The device, the jaw, the jaw assembly, the bladder, the sealing members, or a combination thereof may include one or more standoffs. The one or more standoffs may function to insulate, restrict, and/or prevent opposing jaws and/or sealing members from directly contacting each other to prevent the device from arcing or shorting. The one or more stand offs may be formed from any suitable material having insulating properties such as, for example, Nylon, PEEK, silicon rubber, a ceramic material, or a combination thereof. The one or more stand offs may be located or attached directly to the sealing members. The one or more stand offs may be located or attached directly to one of the bladders, and project beyond a height of the sealing members located on that bladder. The one or more stand offs may be located on only one jaw or support member, or on both opposing jaws or support members.

The jaw assembly, one or more of the jaws, one or more of the support members, the device, or a combination thereof may comprise one or more bladders. The one or more bladders may function to move or reposition the one or more sealing members located on the corresponding one or more bladders by inflating or deflating the corresponding one or more bladders.

The one or more bladders may be inflated by filing or adding fluid to the one or more bladders with fluid from the fluid source. Before the one or more bladders are inflated, the bladder may be completely empty of fluid, or some fluid may be present inside the bladder. Inflating the bladder may cause the bladder to expand or swell due to the fluid pressure inside the bladder.

Inflating the one or more bladders may cause the one or more sealing members located on the corresponding bladders to be moved away from a support member or support surface on which the bladder and sealing members are carried. Inflating the one or more bladders on the lower jaw may cause the one or more sealing members located on the corresponding bladders to be moved up and away from the support member or support surface on which the bladder and sealing members are carried. Inflating the one or more bladders on the upper jaw may cause the one or more sealing members located on the corresponding bladders to be moved down and away from the support member or support surface on which the bladder and sealing members are carried.

Inflating the one or more bladders may move the jaw assembly into the closed configuration. That is, by inflating the bladder, the gap defined between the opposing jaws is reduced or taken up, and a clamping force may be applied or increased on the anatomical feature located between the jaws. Stated another way, one or both of the jaws need not be moved to move the jaw assembly into the closed or gripping configuration; instead, only one or more bladders can be inflated to move the jaw assembly into the closed or gripping configuration.

Inflating the one or more bladders may function to move the one or more sealing members located on the corresponding bladder along a generally uniform path. This means that a proximal end and a distal end of the sealing member is moved along a generally constant path, at substantially the same time, at substantially the same rate or pace, rather than the sealing member tipping or pivoting and one end moving or displacing more or at a faster rate or pace than another end as may be the case when the jaws are pivot or tipped using traditional forceps. By inflating the one or more bladders, a uniform gripping pressure is applied on the anatomical feature between the support members along an entire length of the jaw assembly, between a proximal or throat end and a distal end).

The one or more bladders may be deflated by removing or reducing the amount of fluid inside the one or more bladders. Some or all of the fluid may be removed from inside the bladder during deflating. When deflated, the bladder may shrink or collapse due to the reduced or removed fluid pressure inside the bladder.

Deflating the one or more bladders may cause the one or more sealing members located on the corresponding bladders to be moved closer to or towards a support member or support surface on which the bladder and sealing members are carried. Deflating the one or more bladders on the lower jaw may cause the one or more sealing members located on the corresponding bladders to be moved down and towards the support member or support surface on which the bladder and sealing members are carried. Deflating the one or more bladders on the upper jaw may cause the one or more sealing members located on the corresponding bladders to be moved up and towards the support member or support surface on which the bladder and sealing members are carried.

Deflating the one or more bladders may move the jaw assembly into the open configuration. That is, by deflating the bladder, the gap defined between the opposing jaws is increased, and a clamping force is reduced or removed. Stated another way, one or both of the jaws need not be moved to move the jaw assembly into the open configuration; instead, only one or more bladders can be deflated to move the jaw assembly into the open configuration.

Deflating the bladder may function to move the one or more sealing members located on the corresponding bladder along a generally uniform path. This means that a proximal end and a distal end of the sealing member is moved along a generally constant path, at substantially the same time, at substantially the same rate or pace, rather than the sealing member tipping or pivoting and one end moving or displacing more or at a faster rate or pace than another end as may be the case when the jaws are pivot or tipped using traditional forceps.

Two or more bladders can be individually inflated and deflated. This means that the two or more bladders are individually connect to the fluid source, the pump, or both. This means that one bladder can be inflated, while the other bladder is not inflated; one bladder is inflated while another bladder is deflated; both bladders are inflated; both bladders are deflated; one bladder is deflated while another bladder is neither inflated nor deflated; or a combination thereof.

The bladder may be a balloon. The bladder may be a membrane with a hollow pocket defined therein. The bladder may have a substantially smooth surface, or the surface may be textured to provide additional friction or gripping on an anatomical feature.

The bladder may be formed from a suitable material for use in medical or surgical procedures. The material should be able to withstand heat generated by the one or more sealing members when the device is used in electrosurgery. The material of the bladder may be compliant, non-complaint, or semi-complaint. Compliance refers to flexibility of a material and its ability to be stretched or distended. The material may be think and flexible. The material may be a polymer, such as, for example, polyimide, polyurethane, or polyethylene terephthalate.

The bladder may have a sufficient shape. The bladder may be generally L-shaped and comprise a generally linear longitudinal section and a distal section that is generally perpendicular to the longitudinal section. The bladder may be generally U-shaped and comprise a pair of generally linear longitudinal sections and a distal section that is generally perpendicular to the longitudinal sections. The bladder may be a generally planar structure that is free of notches, gaps, or voids.

The bladder may be located on the support member. The bladder may be attached to the support member. The bladder may be sandwiched between the one or more sealing members and the support member.

The bladder may comprise one or more recesses. The one or more recesses may correspond to a shape of the one or more sealing members located on the bladder. The one or more recesses may function to assist in assembly of the device—i.e., to provide for proper placement of the one or more sealing members on the bladder. The one or more recesses may function to assist in assembly of the device—i.e., to provide for proper placement of the one or more sealing members on the bladder. The one or more recesses may function to partially submerge the one or more recesses into the bladder so that a top or exposed surface of the one or more sealing members is on the same plane as a top or exposed surface of the bladder.

The bladder may be in fluid communication with the fluid source via one or more fluid lines. If there are multiple bladders on one jaw or both jaws, each of the jaws may be in individual communication with the fluid source with a fluid line. If there are multiple bladders on one jaw or both jaws, the jaws may be connected together to the fluid source via a single fluid tube or line.

One or more fluid sources may be in fluid communication with the device or the one or more bladders via one or more fluid lines. The fluid source may comprise a liquid, a gas, or both. The liquid may be saline. The fluid source, the one or more fluid lines, or both may be located on or inside the hand piece or the introducer. The fluid source may be located next to or incorporated into the same housing as the power source. The fluid may be supplied to the one or more bladders to inflate the bladders. The fluid may be withdrawn from the one or more bladders to deflate the bladders. The fluid may be supplied to the one or more bladders by manipulating one or more user controls on the hand piece. The fluid may be supplied to the one or more bladders by manipulating one or more other user controls that are not on the hand piece, such a foot pedal, for example. Fluid may be supplied to or withdrawn from the bladders via a pump located between the fluid source and the device or bladder.

Figure 1:
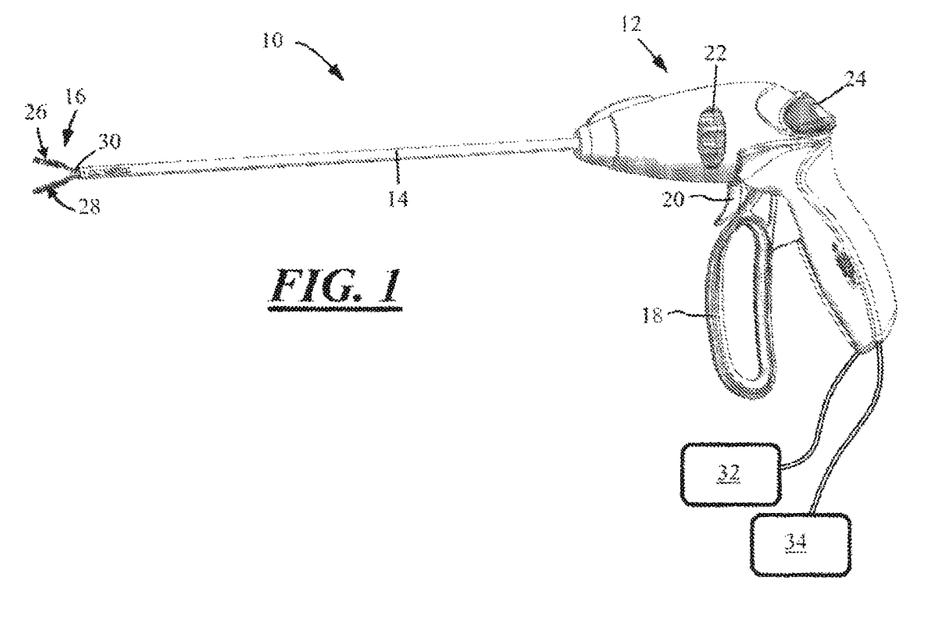
FIG. 1 is a side view of a surgical device having a jaw assembly, the jaw assembly comprises a first jaw and a second jaw.

FIG. 1 illustrates a surgical device 10 that is forceps. The surgical device 10 comprises a hand piece 12, an introducer 14, and a jaw assembly 16. The hand piece 12 comprises a plurality of user controls, including a handle 18, a trigger 20, a wheel 22, and a button 24. The jaw assembly 16 comprises a first jaw 26 and a second jaw 28. The surgical device 10 comprises a cut blade 30 that is located in between the jaws 26, 28. The surgical device 10 may be in communication with a generator 32 and a fluid source 34.

One or more of the user controls 18, 20, 22, 24 may be adapted to move one or both jaws 26, 28 towards or away from the other jaw 26, 28 so that the jaw assembly 16 can be moved between a closed and open configuration. One or more of the user controls 18, 20, 22, 24 may be adapted to move and rotate one or both jaws 26, 28 relative to each other. This is discussed further with reference to FIG. 8. One or more of the user controls 18, 20, 22, 24 may be adapted to provide power from the generator 32 to one or more sealing members or sealing plates on one or both jaws 26, 28. One or more of the user controls 18, 20, 22, 24 may be adapted to provide fluid from the fluid source 34 to one or more of the bladders on one or both jaws 26, 28.

Figure 2:
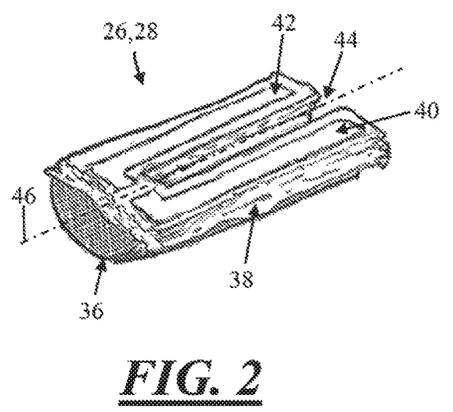
FIG. 2 is a perspective view of a jaw, the jaw can be one or both of the jaws of the jaw assembly of FIG. 1.

FIG. 2 illustrates one or both of the jaws 26, 28. The jaw 26, 28 comprises a support member 36; a bladder 38 located on the support member 36, a first sealing member 40 located on the bladder 38; and a second sealing member 42 located on the bladder 38.

Figure 3:
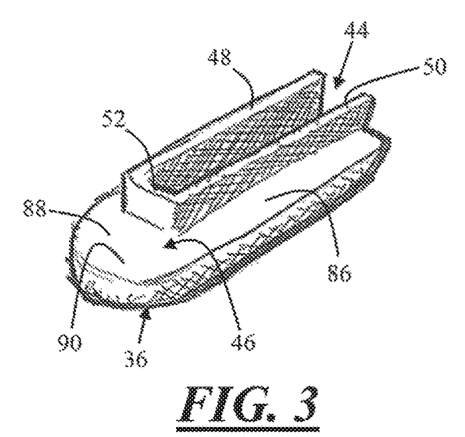
FIG. 3 is a perspective view of a support member of the jaw of FIG. 2.

The support member 36 comprises a notch or blade slot 44, which is illustrated and further described at FIG. 3. The cut blade 30 (FIG. 1) is located in the blade slot 44.

The first sealing member 40 is located on one side of the blade slot 44, and the second sealing member 42 is located on another side of the blade slot 44. Stated another way, the first sealing member 40 is laterally offset to one side of the blade slot 44, and the second sealing member 42 is laterally offset to another side of the blade slot 44. Stated another way, the support member 36, the blade slot 44, and/or the cut blade 30 may extend along a longitudinal axis 46. The first sealing member 40 is located on one side of the longitudinal axis 46, and the second sealing member 42 is located on another side of the longitudinal axis 46.

FIG. 3 illustrates the support member 36. The support member 36 comprises a generally planar U-shaped support surface 46 on which the bladder 38 is located. The support surface 46 comprises a first longitudinal section 86, an opposing section longitudinal section 88, and a nose or distal section 90 that surround the blade slot 44. The blade slot 44 is an absence of material or structure in the support member 36 defined between the sections 86, 88, 90 thus giving the support member 36 a U-shape.

The blade slot 44 also comprises a pair of opposing side walls 48, 50 that project away from the support surface 46. The blade slot 44 comprises a front wall 52 that projects away from the support surface 46, and is arranged generally perpendicular to the opposing side walls 48, 50. The front wall 52 is connected to the opposing side walls 48, 50. The front wall 52 is adapted to restrict or prevent the cut blade 30 from unintentionally contacting and undesirably cutting, puncturing, or otherwise damaging the bladder 36, especially the nose or distal section 58 of the bladder 36 in FIG. 4, or the sections 58A, 58B in FIG. 5, especially when the cut blade 30 is moved or reciprocated in the blade slot 44.

However, in some configurations, the support member 36 may be free of a blade slot 44, and thus the support surface 46 may be a generally continuous planar surface.

Figures 4, 5:
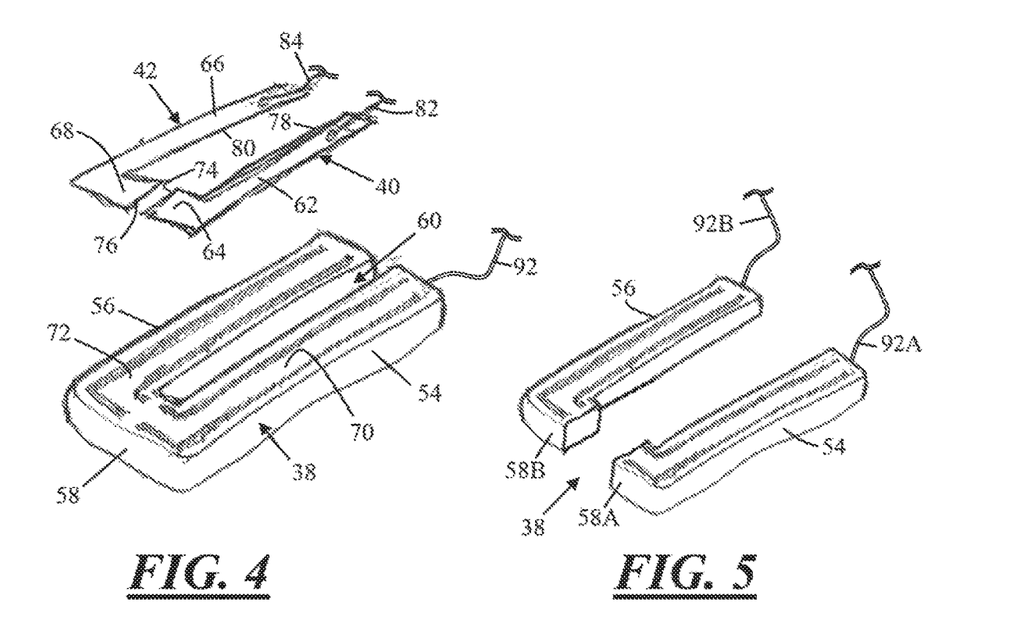
FIG. 4 is an exploded perspective view of a bladder and sealing members of the jaw of FIG. 2.
FIG. 5 is a perspective view of a bladder of the jaw of FIG. 2.

FIG. 4 illustrates the bladder 38 and the first and second sealing members 40, 42.

The bladder 38 comprises a first longitudinal section 54, a second longitudinal section 56, and a nose or distal section 58 that is arranged generally perpendicular to the opposing longitudinal sections 54, 56.

When assembled (i.e., FIG. 2), the first longitudinal section 54 of the bladder 38 is located on the first longitudinal section 86 of the support surface 46 or support member 36; the second longitudinal section 56 of the bladder 38 is located on the second longitudinal section 88 of the support surface 46 or support member 36; and the nose or distal section 58 of the bladder 38 is located on the nose or distal section 90 of the support surface 46 or support member 36.

The bladder 38 comprises a notch 60 defined within or between the sections 54, 56, and 58. When the bladder 38 is located on the support surface 46 of the support member 36, the opposing side walls 48, 50 of the blade slot 44 are located within the notch 60 of the bladder 38. The front wall 52 of the blade slot 44 is adapted to restrict or prevent the cut blade 30 from unintentionally contacting and undesirably cutting, puncturing, or otherwise damaging the nose or distal section 58 of the bladder 36 when the cut blade 30 is moved or reciprocated.

However, in some configurations, the bladder 38 may be free of a notch 60, and thus the bladder 38 may be a generally continuous planar structure. Such a bladder 38 may be used with a support member 36 that is also free of a blade slot 44, and thus has a generally continuous planar surface, as was discussed above referring to FIG. 3.

The bladder 38 is in fluid communication with the fluid source 34 (FIG. 1) via one or more lines 92. The bladder 38 is inflatable by supplying or filling the bladder 38 with fluid from the fluid source 34. The fluid may be a liquid or gas. Inflating the bladder 38 changes a relative position of the first sealing member 40, the second sealing member 42, or both relative to the support member 38.

The first sealing member 40 includes a longitudinal section 62 and a distal section 64 that is generally perpendicular to the longitudinal section 62. The second sealing member 42 includes a longitudinal section 66 and a distal section 68 that is generally perpendicular to the longitudinal section 66. Accordingly, each of the sealing members 40, 42 are generally L-shaped. One or both of the sealing members 40, 42 may, however, only comprise the respective longitudinal sections 62, 66 (i.e., one or both of the distal sections 64, 68 may be removed). One or both of the sealing members 40, 42 may, however, only comprise the respective distal sections 64, 68 (i.e., one or both of the longitudinal sections 62, 66 may be removed).

The bladder 38 may comprise a first depression 70 and a second depression 72. The first depression 70 may have a size and shape that generally corresponds to the first sealing member 40 and is adapted to receive the first sealing member 40. The second depression 72 may have a size and shape that generally corresponds to the second sealing member 42 and is adapted to receive the second sealing member 42. Accordingly, each of the depressions 70, 72 are generally L-shaped.

When the first and second sealing members 40, 42 are located on the bladder 38, the sealing members 40, 42 are arranged closer together at the distal end of the support member 36 or bladder 38 than at a proximal end of the support member 36 or bladder 38. More specifically, a gap defined between opposing adjacent edges 74, 76 of the respective distal sections 64, 68 is smaller than a gap defined between opposing adjacent edges 78, 80 of the respective longitudinal sections 62, 66. The gap defined between the opposing adjacent edges 78, 80 of the respective longitudinal sections 62, 66 is provided to not interfere with the blade slot and blade located in the blade slot. At the distal end of the support member 36, the blade slot and blade are not provided; thus, the sealing members 40, 42 are arranged closer together.

The first sealing plate 40 is electrically connected to a first pole of the generator 32 via a conductor 82, and the second sealing plate 42 is electrically connected to a second pole of the generator 32 via a conductor 84 so that the surgical device 10 is operable as an electrosurgical device, and more particularly, bipolar electrosurgical forceps.

FIG. 5 illustrates another bladder 38. The bladder 38 of FIG. 5 is substantially the same as the bladder 38 illustrated and described above at FIG. 4, except that the bladder 38 of FIG. 5 comprises two discrete pieces. That is, the bladder 38 of FIG. 5 comprises a first longitudinal section 54 that is located on the first longitudinal section 86 of the support surface 46 or support member 36; and a second longitudinal section 56 that is located on the second longitudinal section 88 of the support surface 46 or support member 36. The nose or distal section of the bladder 38 is split into first distal section 58A that is connected to longitudinal section 54 and a second distal section 58B that is connected to longitudinal section 56. The nose or distal sections 58A, 58B are located on the nose or distal section 90 of the support surface 46 or support member 36.

Each of the longitudinal sections 54, 56 are in fluid communication with the fluid source 34 (FIG. 1) via one or more corresponding lines 92A, 92B. The bladder 38 of FIG. 5 may be advantageous in that the longitudinal sections 54, 56 of the bladder 38 can be individually inflated and/or controlled, which means that a position of the first sealing member 40 and the second sealing member 42 relative to the support member 38 can be individually adjusted or controlled.

Figure 6:
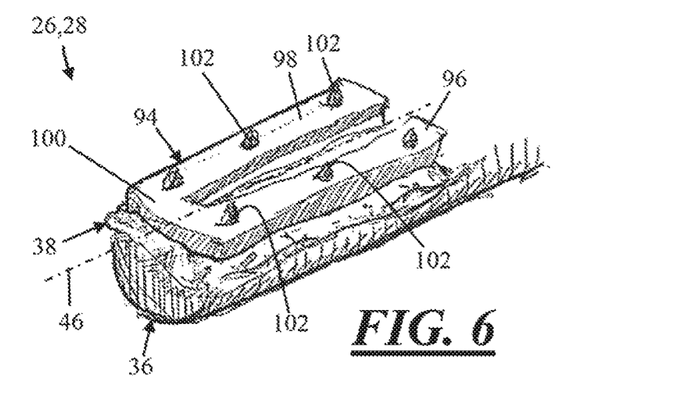
FIG. 6 is a perspective view of a jaw, the jaw can be one or both of the jaws of the jaw assembly of FIG. 1.

FIG. 6 illustrates one or both of the jaws 26, 28. The jaw 26, 28 comprises a support member 36; a bladder 38 located on the support member 36; and a sealing plate 94 located on the bladder 38.

The support member 36 may be substantially similar to the support member 36 described above and illustrated at FIG. 3; therefore, in the interest of brevity, its structure and features will not be repeated again. The support member 36 of FIG. 5 may or may not include the blade slot.

The bladder 38 may be substantially similar to the bladder 38 described above and illustrated at either FIG. 4 or 5; therefore, in the interest of brevity, its structure and features will not be repeated again. The bladder 38 of FIG. 5 may or may not include the notch 60 like in FIG. 4.

The sealing plate 94 comprises a generally U-shaped structure. More specifically, the sealing plate 94 comprises a first sealing member 96 or longitudinal section located on one side of the blade slot of the support member 36 (FIG. 3), a second sealing member 98 or longitudinal section located on another side of the blade slot of the support member 36, and a distal section 100 that is generally perpendicular to the sealing members 96, 98 or longitudinal sections. A notch is defined between the sections 96, 98, 100. The notch of the sealing plate 94 is generally aligned with the blade slot defined in the support member 36, and the notch defined in the bladder 38 so that the cut blade can be moved therein.

Stated another way, the support member 36, the blade slot 44, and/or the cut blade 30 may extend along a longitudinal axis 46, and the first sealing member 96 or longitudinal section is located on one side of the longitudinal axis 46, and the second sealing member 98 or longitudinal section is located on another side of the longitudinal axis 46.

The sealing plate 94 comprises one or more spacers 102. The spacers 102 are non-conductive or insulating features that project away from the sealing plate 94 to prevent accidental or unintended shorting of the device 10 if the support member 26, 28 or jaw contacts an opposing support member 26, 28 or jaw while a therapeutic power was being communicated the device 10 from the generator 32. While not illustrated in FIGS. 2 and 4, one or both of the sealing members 40, 42 may include one or more of these spacers 102.

Figure 7:
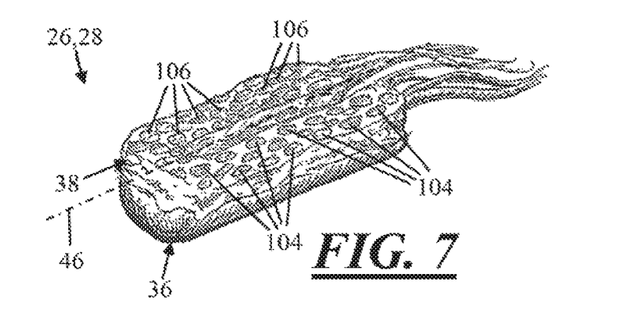
FIG. 7 is a perspective view of a jaw, the jaw can be one or both of the jaws of the jaw assembly of FIG. 1.

FIG. 7 illustrates one or both of the jaws 26, 28. The jaw 26, 28 comprises a support member 36; a bladder 38 located on the support member 36; one or more first sealing members 104; and one or more second sealing members 106.

The support member 36 may be substantially similar to the support member 36 described above and illustrated at FIG. 3; therefore, in the interest of brevity, its structure and features will not be repeated again. The support member 36 of FIG. 6 may or may not include the blade slot.

The bladder 38 may be substantially similar to the bladder 38 described above and illustrated at either FIG. 4 or 5; therefore, in the interest of brevity, its structure and features will not be repeated again. The bladder 38 of FIG. 6 may or may not include the notch.

The sealing members 104, 106 may be printed onto a surface of the bladder 38. Each of the sealing members 104, 106 may be in electrical communication with a pole of the generator 32 (FIG. 1) via discrete electrical conductors. The one or more first sealing members 104 are located on one side of the blade slot 44 of support member 36 (FIG. 3), and the one or more second sealing members 106 are located on another side of the blade slot 44. Stated another way, the one or more first sealing members 104 are laterally offset to one side of the blade slot 44, and the one or more second sealing members 106 are laterally offset to another side of the blade slot 44. Stated another way, the support member 36, the blade slot 44, and/or the cut blade 30 may extend along a longitudinal axis 46, and the one or more first sealing members 104 are located on one side of the longitudinal axis 46, and the one or more second sealing members 106 are located on another side of the longitudinal axis 46.

Figure 8:
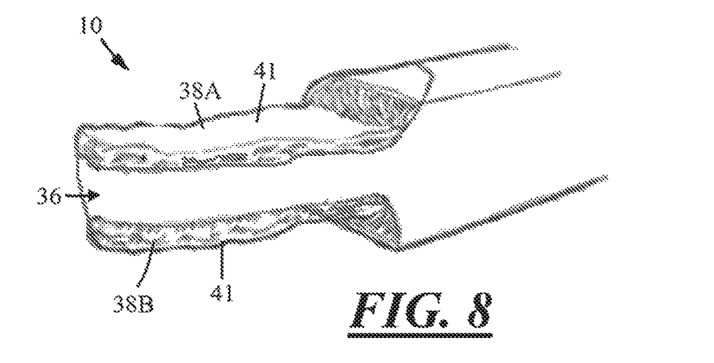
FIG. 8 is a perspective view of a surgical device that is a spatula.

FIG. 8 illustrates a surgical device 10 that is a spatula. The surgical device 10 comprises a support member 36; a first bladder 38A located on one side of the support member 36; and a second bladder 38B located on an opposing second side of the support member 36. The support member 36 is sandwiched between the two bladders 38A, 38B. In some configurations, the spatula includes only one bladder, either bladder 38A or 38B. The bladders 38A, 38B may be controlled together (i.e., inflated and deflated simultaneously) or the bladders 38A, 38B can be individually controlled (i.e., inflated and deflated independently of each other).

The support member 36 of FIG. 8 may be like the support member 36 illustrated and described at FIG. 3; or the support member 36 of FIG. 8 may be free of a blade slot 44 and thus may be a single, continuous pad or support without any slots or notches.

One or both of the bladders 38A, 38B of FIG. 8 may be like the bladders illustrated and described at FIGS. 4 and 5; or one or both of the bladders 38A, 38B of FIG. 8 may be free of a notch 60 and instead may be a single, continuous bladder pad having a planar surface located on a corresponding single continuous support member pad or support.

The surgical device 10 or spatula may comprise one or more sealing members 41 located on one or both of the bladders 38A, 38B. The sealing members 41 may be like the sealing members illustrated and described at FIG. 2, FIG. 4, and/or FIG. 7.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A surgical device comprising:
    a first support member;
    a bladder located on the first support member;
    a first sealing member located on the bladder; and
    a second sealing member located on the bladder;
    wherein the bladder is inflatable, and inflating the bladder changes a position of the first sealing member, the second sealing member, or both relative to the first support member.

2. The surgical device of claim 1, wherein the first support member comprises a slot.

3. The surgical device of claim 2, wherein the slot comprises a blade slot.

4. The surgical device of claim 3, further comprising a blade located in the blade slot.

5. The surgical device of claim 3, wherein the first sealing member is located on one side of the blade slot.

6. The surgical device of claim 5, wherein the second sealing member is located on another side of the blade slot.

7. The surgical device of claim 1, further comprising a second support member.

8. The surgical device of claim 7, wherein the surgical device is forceps.

9. The surgical device of claim 8, wherein the first support member is a first jaw of the forceps and wherein the second support member is a second jaw of the forceps.

10. The surgical device of claim 1, wherein the surgical device comprises a sealing plate, the first sealing member is a first longitudinal section of the sealing plate, and the second sealing member is a second longitudinal section of the sealing plate.

11. The surgical device of claim 1, wherein the first sealing member and the second sealing member are discrete sealing members.

12. The surgical device of claim 1, wherein at least one of the first sealing member or the second sealing member comprises a longitudinal section and a distal section, and wherein the distal section is generally perpendicular to the longitudinal section.

13. The surgical device of claim 1, wherein both the first sealing member and the second sealing member are generally L-shaped.

14. The surgical device of claim 1, wherein the first and second sealing members are arranged on the bladder closer together at a distal end of the first support member than at a proximal end of the first support member.

15. The surgical device of claim 1, wherein the first sealing member and the second sealing member are arranged on a common plane.

16. The surgical device of claim 1, wherein the bladder comprises a first depression for receiving the first sealing member and a second depression for receiving the second sealing member.

17. A surgical device comprising:
a support member extending along a longitudinal axis and including a generally planar support surface;
a bladder located on one side of the support member and including a generally planar bladder surface;
a first sealing member located on the bladder, the first sealing member disposed on one side of the longitudinal axis; and
a second sealing member located on the bladder, the second sealing member disposed on another side of the longitudinal axis;
wherein the bladder is inflatable, and inflating the bladder changes a position of the first sealing member, the second sealing member, or both relative to the support member.

18. The surgical device of claim 17, wherein the first sealing member and the second sealing member are discrete electrodes printed onto the bladder.

19. The surgical device of claim 17, further comprising a second bladder located on an opposing side of the support member.

20. A surgical device comprising:
a support member including an opening for a cutting element, the support member and the opening extending along a longitudinal axis;
a bladder located on the support member;
a first sealing member located on the bladder, the first sealing member positioned on one side of the longitudinal axis; and
a second sealing member located on the bladder, the second sealing member positioned on another side of the longitudinal axis;
wherein the bladder is inflatable, and inflating the bladder changes a position of the first sealing member, the second sealing member, or both relative to the support member.

* * * * *